(12) United States Patent
Lavrentyev et al.

(10) Patent No.: US 9,234,878 B2
(45) Date of Patent: Jan. 12, 2016

(54) COMPONENT INSPECTION USING A CURVED TRANSDUCER ARRAY

(75) Inventors: Anton I. Lavrentyev, Cromwell, CT (US); Jeffrey A. Umbach, Palm Beach Gardens, FL (US)

(73) Assignee: United Technologies Corporation, Hartford, CT (US)

( * ) Notice: Subject to any disclaimer, the term of this patent is extended or adjusted under 35 U.S.C. 154(b) by 480 days.

(21) Appl. No.: 13/353,875

(22) Filed: Jan. 19, 2012

(65) Prior Publication Data

US 2013/0191042 A1    Jul. 25, 2013

(51) Int. Cl.
| | | |
|---|---|---|
| G01N 29/22 | (2006.01) |
| G01N 29/04 | (2006.01) |
| G01N 29/24 | (2006.01) |
| G01N 29/26 | (2006.01) |
| G10K 11/34 | (2006.01) |
| G01S 15/89 | (2006.01) |
| G10K 11/32 | (2006.01) |

(52) U.S. Cl.
CPC ............ *G01N 29/221* (2013.01); *G01N 29/043* (2013.01); *G01N 29/2456* (2013.01); *G01N 29/262* (2013.01); *G01S 15/892* (2013.01); *G01S 15/8922* (2013.01); *G01S 15/8925* (2013.01); *G01S 15/8929* (2013.01); *G10K 11/32* (2013.01); *G10K 11/34* (2013.01); *G01N 2291/106* (2013.01)

(58) Field of Classification Search
CPC .......... G01N 29/262; G01N 2291/106; G01N 2291/0422; G01N 2291/044; G01N 2291/2693; G01N 29/043; G01N 2291/0231; G01N 2291/02854; G01N 2291/0421; G01N 2291/0428; G01N 2291/2623; G01N 29/0609; G01N 29/07; G01N 29/28; G01N 29/30; G10K 11/34; G10K 11/346; A61B 8/14; B61K 9/10; G01S 15/8909; G01S 7/52095
USPC .......................................................... 702/39
See application file for complete search history.

(56) References Cited

U.S. PATENT DOCUMENTS

| | | | |
|---|---|---|---|
| 4,276,779 A | 7/1981 | Davis, Jr. | |
| 6,310,831 B1 | 10/2001 | Dillman | |
| 6,312,386 B1 | 11/2001 | Bolorforosh et al. | |
| 7,010,982 B2 | 3/2006 | Bergman | |
| 7,305,885 B2 | 12/2007 | Barshinger et al. | |
| 7,428,842 B2 | 9/2008 | Fair et al. | |
| 2002/0139193 A1* | 10/2002 | Angelsen ............. | B06B 1/0625 73/602 |
| 2006/0103267 A1* | 5/2006 | Lupien ................. | B60B 1/0625 310/334 |
| 2011/0066032 A1* | 3/2011 | Vitek .................... | A61N 7/02 600/459 |
| 2011/0126626 A1* | 6/2011 | Koch .................... | G01N 29/07 73/632 |
| 2011/0237950 A1 | 9/2011 | Meng | |

OTHER PUBLICATIONS

Lamarre, "Dynamic Focusing of Phased Arrays for Nondestructive Testing: Characterization and Application," NDT.net—Sep. 1999, vol. 4 No. 9 (http://www.ndt.net/article/v04n09/lamarre/lamarre.htm).*
Roberts, Ron A., Optimization of Transmission Filed for DDF-Based Phased-Array Inspection, AIP Conference Proceedings, vol. 820 (2006), pp. 813-820.
Extended European Search Report for EP Application No. 13150407.8 dated Mar. 17, 2015.

* cited by examiner

*Primary Examiner* — Alexander H Taningco
*Assistant Examiner* — Seokjin Kim
(74) *Attorney, Agent, or Firm* — Carlson, Gaskey & Olds, P.C.

(57) ABSTRACT

An example component inspection method includes directing a wave from a curved array of transducer elements toward a component. The method forms the wave using focal law calculator software.

17 Claims, 4 Drawing Sheets

COMPONENT INSPECTION USING A CURVED TRANSDUCER ARRAY

BACKGROUND

This disclosure relates generally to inspecting and, more particularly, to controlling a beam from a curved transducer array.

Phased array inspection tools are well-known. One of the tools is a phased array probe. Phased array probes typically consist of an array of transducer elements. Each of the individual transducer elements can be pulsed (excited) separately. The pulses cause transducer elements to generate sound waves that combine to form a sound beam that propagates through a component. Potential defects in the component reveal themselves by reflecting the sound beam back to the transducer.

Typical phased array systems include flat (non-curved) arrays of transducer elements. These arrays of transducer elements constitute a flat (non-curved) surface of a probe. The timing of pulsing (or exciting) individual transducer elements is phased or varied. The phasing changes how the sound waves from transducer elements combine with each other. The phasing steers and shapes the sound beam. Flat probes, however, are not well-suited for inspecting many components, especially components having relatively complex geometries.

SUMMARY

An example component inspection method includes directing a wave from a curved array of transducer elements toward a component. The method forms the wave using focal law calculator software.

An example component inspection method includes directing a wave from a transducer array toward a component. The transducer array is curved. The method uses focal law calculator software to determine the phasing of the elements in order to focus the wave, stretch the wave, steer the wave, or some combination of these.

An example phased array inspection system includes a curved array of transducer elements. A computer uses a focal law calculator to calculate focal law files. A controller controls a wave generated by a curved array of transducer elements based on the focal law files.

DESCRIPTION OF THE FIGURES

The various features and advantages of the disclosed examples will become apparent to those skilled in the art from the detailed description. The figures that accompany the detailed description can be briefly described as follows.

DETAILED DESCRIPTION

Figure 1:
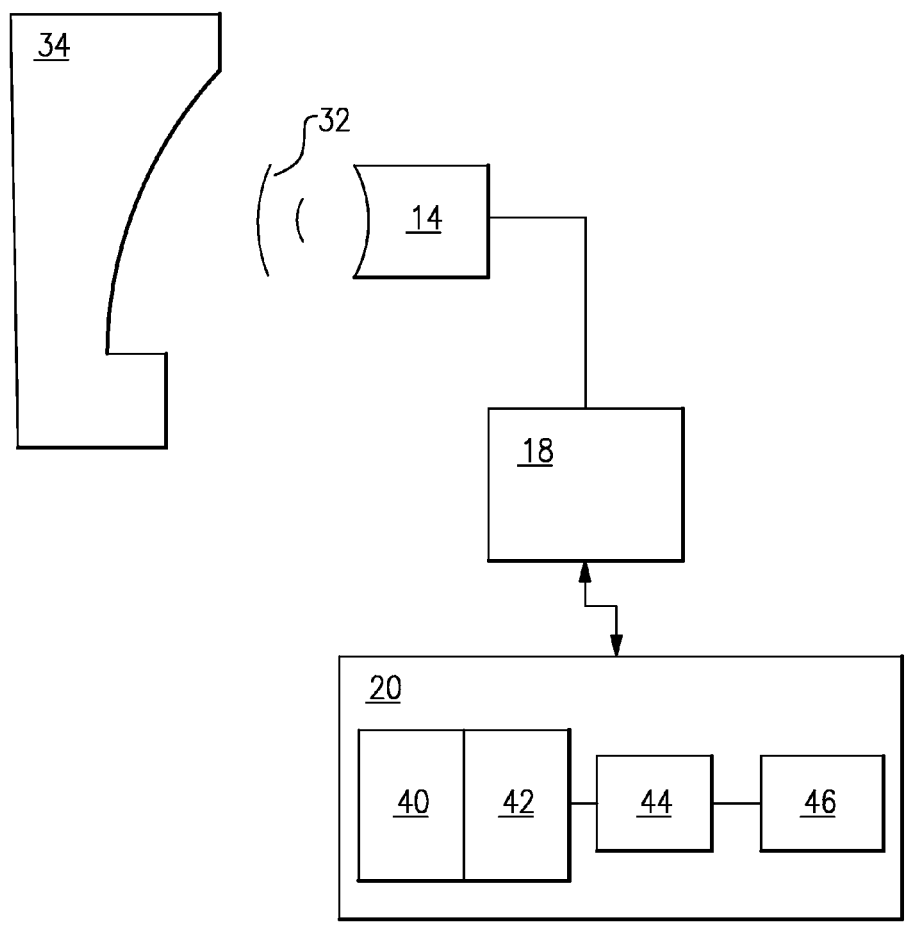
FIG. 1 shows a highly schematic view of an example phased array inspection system incorporating a curved probe.
Figure 2A:
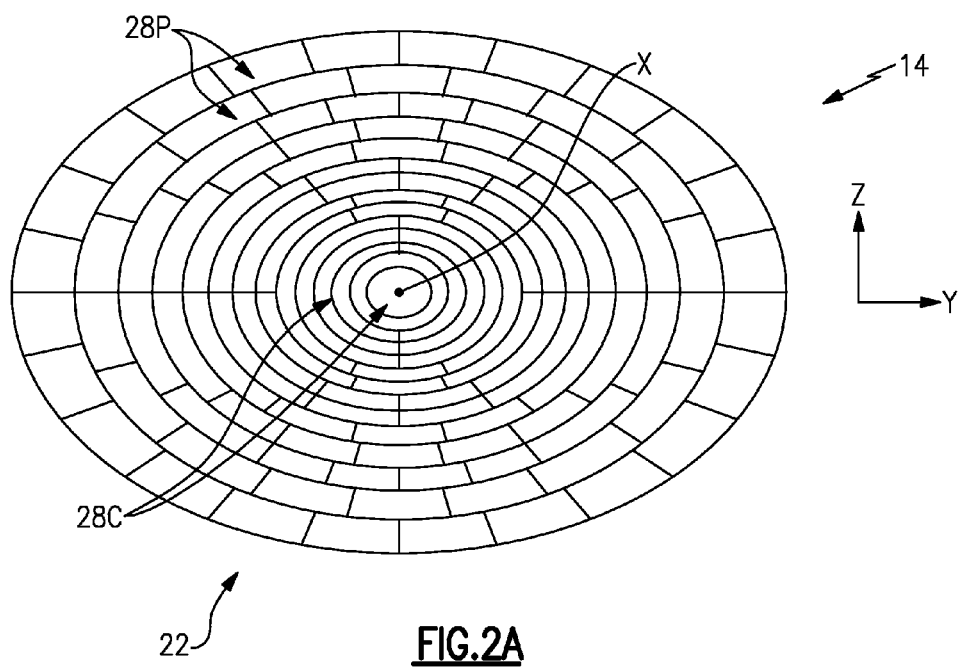
FIG. 2A shows a front view of an example curved probe for use in the FIG. 1 phased array inspection system.
Figure 2B:
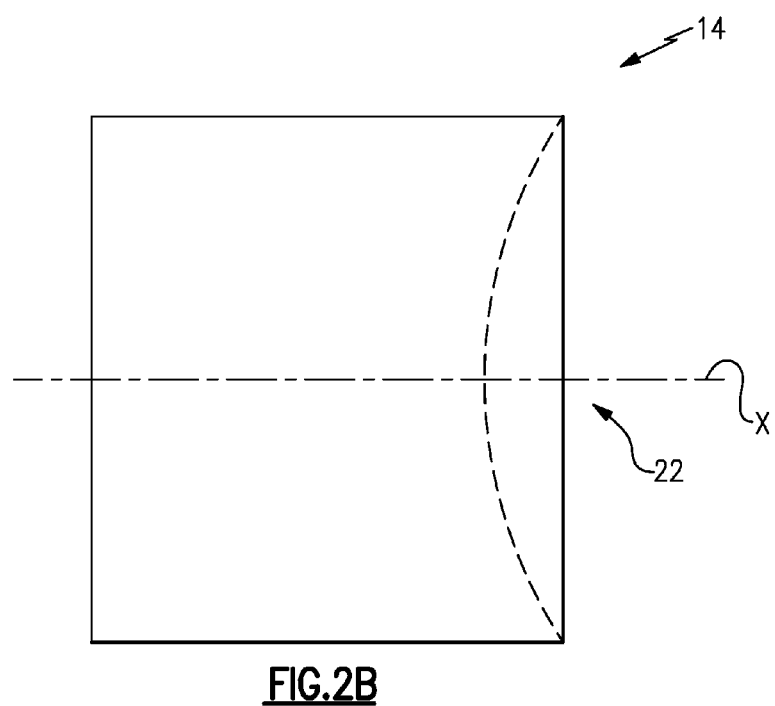
FIG. 2B shows a side view of the FIG. 2A curved probe in a second plane perpendicular to the first plane.

Referring to FIGS. 1 to 2B, an example phased array inspection system 10 includes a probe 14 coupled to a controller 18. An outer surface of the probe 14 includes a curved transducer array 22. The probe 14 is considered a curved probe because of the curved transducer array 22.

The curved transducer array 22 includes multiple individual transducer elements 28. Each of the transducer elements 28 can be pulsed (excited) to generate a sound wave. Sound waves generated by the transducer elements 28 combine to form a sound beam 32 that propagates from the curved transducer array 22.

During an inspection procedure, the beam 32 is directed toward the component 34. In one example, the probe 14 and the component 34 are both submerged within a tank of water. The water facilitates transmission of the beam 32.

Portions of the beam 32 are reflected toward the curved transducer array 22 after encountering a defect, inclusion, void, etc. within the component 34. The curved transducer array 22 receives the reflected portions of the beam 32, which are analyzed in a known way to reveal the defect, inclusion, void, etc.

In this example, component 34 is a new or used component, such as a turbine disk in a high pressure turbine section of a turbomachine. Other examples may be used with other types of turbomachine components and components other than turbomachine components. The system 10 could be used with any component or material that will be further processed to produce a component needing an inspection.

The example curved transducer array 22 is particularly useful for inspecting the component 34 because the curvature of the curved transducer is designed to facilitate formation of an appropriate sound beam inside component 34. Flat (non-curved) arrays of transducers often cannot generate an appropriate sound beam in (typically curved) turbomachine components.

The example curved transducer array 22 is curved in three directions. That is, the curved transducer array 22 is curved relative to axes X, Y, and Z. (In FIG. 2A, axis X extends outward from the page.) Other example probes are curved in at least two directions.

The curved transducer array 22 includes transducer elements 28C near the center of the probe 14 (relative to the axis X) and transducers elements 28P that are near the radial perimeter of the probe 14. In this example, focal law calculator software utilizes coordinates of the transducer elements 28C and 28P to form a beam propagating from the curved transducer array 22.

The example controller 18 is a stand-alone electronic device that is controlled by an external control software 44 running on a stand-alone personal computer 20. The control software 44 uses internally or externally generated focal laws that define how and when individual elements of an array are excited and how data received by individual array elements is processed.

A focal law software 46 generates focal laws that are used by the control software 44. The focal law software 46 is considered a focal law calculator in this example.

The example personal computer 20 includes a memory portion 40 and a processor 42. The focal law software 46 produces focal law files. The control software 44 uses focal law files and produces phasing commands that are stored in the memory portion 40 and are sent by the processor 42 to the controller 18. The controller 18 executes phasing commands and thus controls how the sound beam 32 is formed by controlling how and when the transducer elements 28 generate pulses.

The example focal law software 46 is a focal law calculator that generates focal law files. The control software 44 uses the focal law files and sends appropriate commands to the controller 18 that excite elements of the curved transducer array 22 to form the sound beam 32. Examples of beam forming include stretching the sound beam 32, steering the sound beam 32, and focusing the sound beam 32.

In this example, the sound beam 32 is stretched during the transmission or generation of a sound beam. Dynamic Depth Focusing (DDF) occurs upon reception of the reflected sound beam. DDF involves combining reflected waves. In the prior art, standard 'off-the-shelf' focal law calculators do not have capability to form focused or stretched beams for a generally curved phased array probe. They also cannot program DDF for generally curved probes.

In this example, stretching the sound beam 32 may involve a positive stretch or a negative stretch. Positive and negative are determined with reference to a nominal focus distance and whether central elements are focused closer or father than 'outer rim' elements.

Figure 3A:
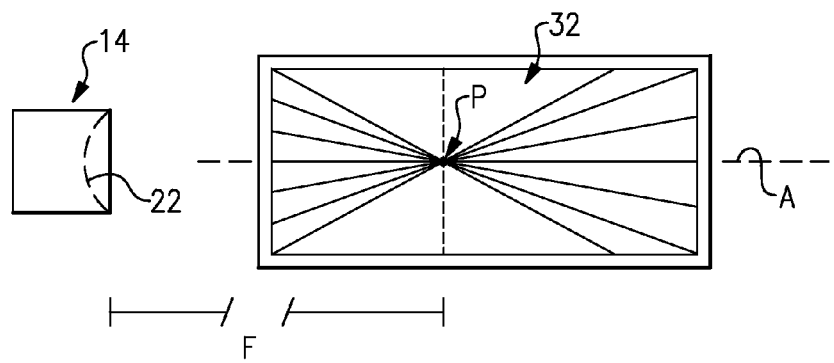
FIG. 3A shows a schematic of a focused beam formation.
Figure 3B:
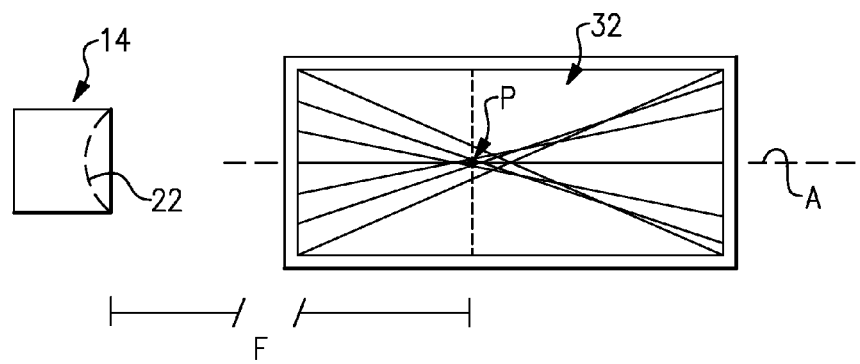
FIG. 3B shows a schematic for a beam with a positive stretch.
Figure 3C:
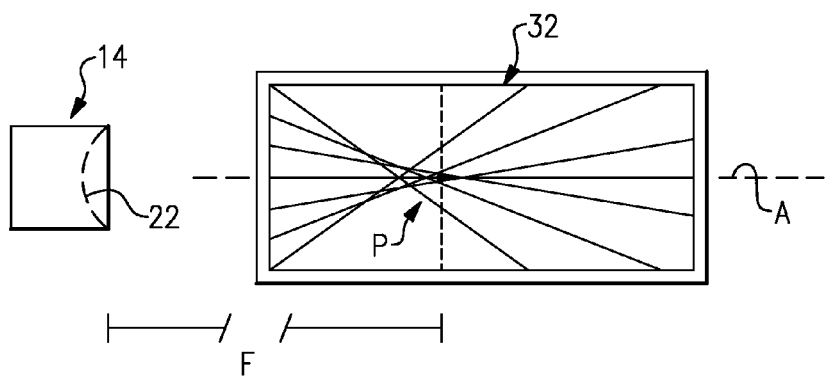
FIG. 3C shows a schematic for a beam with a negative stretch.
Figure 4A:
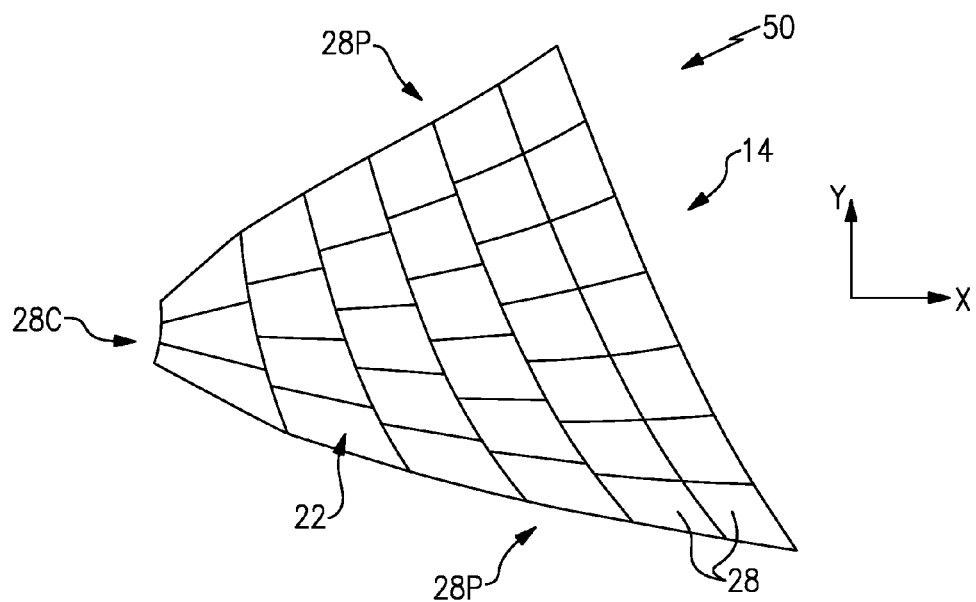
Figure 4B:

For example, referring to FIGS. 3A to 3C with continuing reference to FIGS. 1 to 2B, a nominal focus distance F is this distance between the transducer array 22 and a point P when the transducer elements 28 are focused on the point P.

The individual transducer elements 28 of the array 22 produce rays that combine to form the beam 32. In the FIGS. 3A-3C, the size of the beam 32 relative to the array 22 has been increased for clarity. FIG. 3A shows the beam focused on the point P. A positive stretch of the beam 32 is achieved when the transducer elements 28C are refocused at a distance less than the nominal focus distance F, and the transducer elements 28P refocused at a distance greater than the nominal focus distance F. Thus, when the beam 32 is positively stretched, waves from the transducer elements 28C intersect an axis A of the beam 32 closer to the probe 14 than the waves from the transducer elements 28P. FIG. 3B shows a positive stretch of the beam 32.

A negative stretch of the beam 32 is achieved when the transducer elements 28C are refocused at a distance greater than the nominal focus distance F, and the transducer elements 28P—at a distance less than the nominal focus distance F. Thus, when the beam 32 is negatively stretched, waves from the transducer elements 28C intersect an axis A of the beam 32 further from the probe 14 than the waves from the transducer elements 28P. FIG. 3C shows a negative stretch of the beam 32.

In this example, focal law calculator software 46 executes the stretching $F_n$ according to the algorithm (1).

$$F_n = F + D_{str} \cdot \left( \frac{n-1}{N-1} - \frac{1}{2} \right) \quad (1)$$

In algorithm (1), F is the nominal focus distance, $D_{str}$ is a desired amount of stretch, n is a number of the transducer element rings 28 within the curved transducer array 22, and N is a total number of element rings within the curved transducer array 22. In this example, the algorithm (1) is utilized with annular arrays of transducer elements such as the array 22.

In this example, the focal law software 46 includes a portion executing the algorithm (1) to stretch the beam 32.

Another way the focal law software 46 may stretch the beam 32 is by controlling the distribution of focal points of the waves from the transducers elements 28 within the curved transducer array 22. The focal law software 46 may use the algorithm (2) to control the focal points.

$$F_n = F_1 + \sum_{j=1}^{n} \Delta F_j, n = 1, N-1, \text{ where} \quad (2)$$

$$F_1 + F - \frac{D_{str}}{2} \cdot \Delta F_j = \frac{D_{str}}{N-1} \left( (2-\xi) + 2(\xi-1)\frac{j-1}{N-1} \right).$$

In the algorithm (2), $\xi$ corresponds to stretch uniformity. When $\xi=1$, focusing distribution is uniform (FIG. 3A). When $\xi=2$, distribution is denser near the far end of the range (FIG. 3B), when $\xi=0$ focusing is denser near the near end of the range.

The preceding description is exemplary rather than limiting in nature. Variations and modifications to the disclosed examples may become apparent to those skilled in the art that do not necessarily depart from the essence of this disclosure. Thus, the scope of legal protection given to this disclosure can only be determined by studying the following claims.

We claim:

1. A component inspection method comprising:
   directing a wave from a curved array of transducer elements toward a component;
   forming the wave using a focal law calculator software, wherein the curved array of transducer elements is curved in at least three dimensions; and
   stretching the wave using the focal law calculator software, wherein the focal law calculator software stretches the wave using an algorithm:

$$F_n = F + D_{str} \cdot \left( \frac{n-1}{N-1} - \frac{1}{2} \right),$$

wherein $F_n$ is the amount of stretching, F is the nominal focus distance, $D_{str}$ is a desired amount of stretch, n is a number of transducer elements within the transducer array, and N is a total number of elements within the transducer array.

2. The component inspection method of claim 1, including dynamic depth focusing the wave using the focal law calculator software.

3. The component inspection method of claim 1, including steering the wave using the focal law calculator software.

4. The component inspection method of claim 1, wherein the curved array of transducer elements forms a portion of a phased array inspection system.

5. The component inspection method of claim 1, wherein a surface of the curved array of transducers is curved.

6. A component inspection method comprising:
   directing a wave from a transducer array toward a component along an axis, the transducer array being curved in at least three dimensions; and
   using a focal law calculator software to focus the wave, stretch the wave, and steer the wave, wherein the focal law calculator software stretches the wave using an algorithm:

$$F_n = F + D_{str} \cdot \left( \frac{n-1}{N-1} - \frac{1}{2} \right),$$

wherein $F_n$ is the amount of stretching, F is the nominal focus distance, $D_{str}$ is a desired amount of stretch, n is a number of transducer elements within the transducer array, and N is a total number of elements within the transducer array.

7. The component inspection method of claim 6, wherein the transducer array forms a portion of a phased array inspection system.

8. The component inspection method of claim 6, wherein the focal law calculator software is executed on a computer.

9. A phased array inspection system, comprising:
a curved array of transducer elements; and
a computer that uses a focal law calculator to calculate focal law files, wherein a controller controls a wave generated by the curved array of transducer elements based on the focal law files, wherein the curved array of transducer elements is curved in at least three dimensions, wherein the focal law calculator software stretches the wave using an algorithm:

$$F_n = F + D_{str} \cdot \left( \frac{n-1}{N-1} - \frac{1}{2} \right),$$

wherein $F_n$ is the amount of stretching, F is the nominal focus distance, $D_{str}$ is a desired amount of stretch, n is a number of transducer elements within the transducer array, and N is a total number of elements within the transducer array.

10. The phased array inspection system of claim 9, wherein the controller dynamic depth focuses the wave based on the focal law files.

11. The phased array inspection system of claim 9, wherein the controller stretches the wave based on the focal law files.

12. The phased array inspection system of claim 9, wherein the controller steers the wave based on the focal law files.

13. The phased array inspection system of claim 9, including a probe, wherein an outwardly facing surface of the probe includes a curved array of transducer elements.

14. The component inspection method of claim 3, wherein the steering includes moving the wave from propagating along a first axis to propagating along a second axis different than the first axis.

15. The component inspection method of claim 6, wherein the stretching includes moving a focus of the wave back and forth along a first axis, and the steering includes moving the wave from propagating along a first axis to propagating along a second axis different than the first axis.

16. A component inspection method, comprising:
directing a wave from a transducer array toward a component along an axis, the transducer array being curved in at least three dimensions; and
using a focal law calculator software to focus the wave, stretch the wave, and steer the wave,
wherein the focal law calculator software controls a distribution of focal points of the waves from the transducer array to stretch the wave, the control provided by using an algorithm:

$$F_n = F_s + \sum_{j=1}^{n} \Delta F_j, n = 1, N-1, \text{ where}$$

$$F_s = F - \frac{D_{str}}{2}, \Delta F_j = \frac{D_{str}}{N-1}\left((2-\xi) + 2(\xi-1)\frac{j-1}{N-1}\right),$$

wherein $F_n$ is the amount of stretching, F is the nominal focus distance, $D_{str}$ is a desired amount of stretch, n is a number of transducer elements within the transducer array, and N is a total number of elements within the transducer array, and $\xi$ is a stretch uniformity.

17. The phased array inspection system of claim 9, wherein the focal law calculator moves the wave in a direction that is transverse to the axis to steer the wave.

* * * * *